United States Patent [19]

Markezich

[11] 3,992,406
[45] Nov. 16, 1976

[54] PREPARATION OF AROMATIC BISIMIDES

[75] Inventor: Ronald L. Markezich, Scotia, N.Y.

[73] Assignee: General Electric Company, Schenectady, N.Y.

[22] Filed: Apr. 14, 1976

[21] Appl. No.: 676,993

[52] U.S. Cl. ............................ 260/326 N; 260/326 S
[51] Int. Cl.² ........................................ C07D 209/48
[58] Field of Search ..................... 260/326 N, 326 S

[56] References Cited
UNITED STATES PATENTS

| | | | |
|---|---|---|---|
| 3,829,428 | 4/1975 | Heath et al. | 260/326 N |
| 3,847,867 | 11/1974 | Heath et al. | 260/47 CP |
| 3,922,284 | 11/1975 | Heath et al. | 260/326 N |

*Primary Examiner*—Lewis Gotts
*Assistant Examiner*—S. P. Williams
*Attorney, Agent, or Firm*—Joseph T. Cohen; Jerome C. Squillaro

[57] ABSTRACT

Aromatic bisimides can be prepared by effecting reaction between a 3- or 4-nitro-N-substituted phthalimide with an aromatic dihydroxy compound in the presence of a certain class of solid alkali-metal fluorides and using a dipolar aprotic compound as a solvent.

8 Claims, No Drawings

PREPARATION OF AROMATIC BISIMIDES

This invention relates to the preparation of aromatic bisimides by the process of effecting reaction between a 3- or 4-nitro-N-substituted phthalimide with an aromatic dihydroxy compound in the presence of a certain class of solid alkalimetal fluorides and using a dipolar aprotic compound as a solvent.

More particularly, the invention is concerned with a process for making aromatic bisimides of the general formula

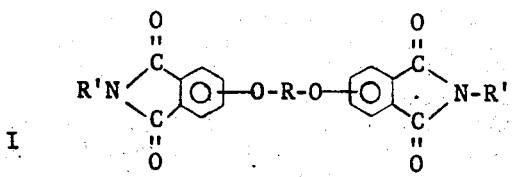

I which process comprises effecting reaction in the presence of a solid alkali-metal fluoride selected form the class consisting of potassium, cesium and rubidium fluorides and mixtures thereof (hereinafter referred to as "alkali-metal fluoride") between a nitro-N-substituted phthalimide of the general formula

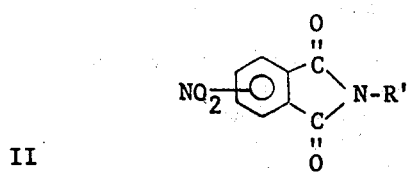

II with an aromatic dihydroxy compound of the general formula

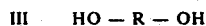

III  HO — R — OH where R is a member selected from the class consisting of (a) divalent radicals of the formula

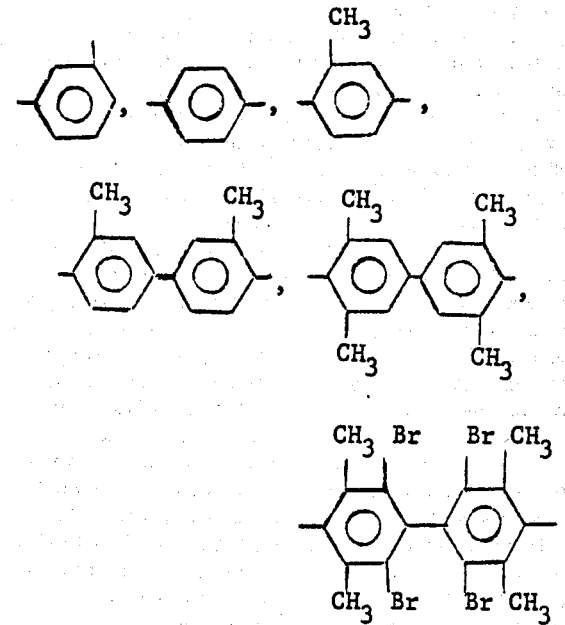

and

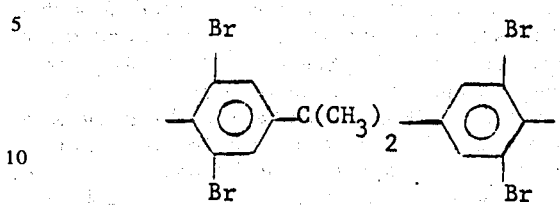

and (b) divalent organic radicals of the general formula

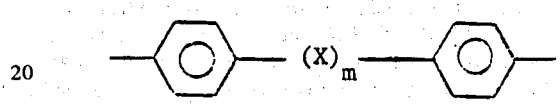

where X is a member selected from the class consisting of divalent radicals of the formulas

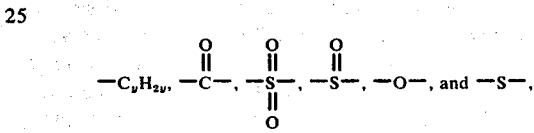

where $m$ is 0 or 1, $y$ is a whole number from 1 to 5, and R' is the phenyl radical or an alkyl radical of from 1 to 2 carbon atoms, the said reaction being conducted in a dipolar aprotic solvent selected from the class consisting of dimethyl sulfoxide, N,N-dimethyl acetamide, N,N-dimethyl formamide (DMF), N-methyl pyrrolidone, and mixtures of such solvents.

Dianhydrides of the general formula

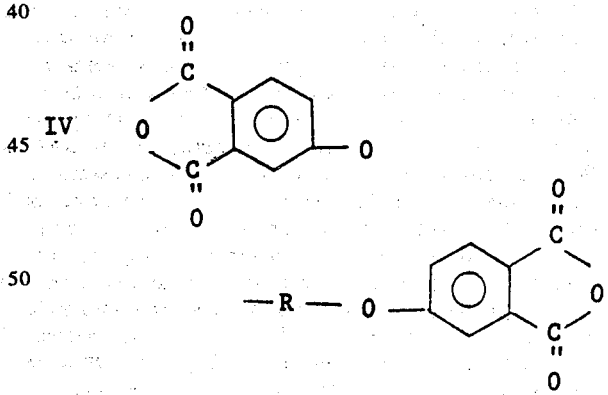

IV where R has the meanings given above have been used in the preparation of polymeric compositions by reacting the aforesaid dianhydrides with various organic diamines in the manner described in U.S. Pat. No. 3,847,867, issued Nov. 12, 1974, and assigned to the same assignee as the present invention which patent by reference is made part of the disclosures and teachings of the instant application. One of the important objectives in making these resins is to insure that the reactants required for such polymeric compositions are made as economically as possible in order that the ultimate cost of the resinous compositions will also be the lowest possible cost.

Several methods have been employed in the past for making the aforesaid aromatic bisimides of formula I. One method for making these aromatic bisimides comprises reacting a nitrophthalimide of formula II, with a dialkalimetal salt (dianion) of a dihydroxy aromatic compound, such as bisphenol-A [ (2,2-bis-4-hydroxyphenyl)propane] to form the derivative of formula I. Thereafter, this bisimide can be treated with aqueous sodium hydroxide in water to form the corresponding tetracarboxylic acid and by suitable treatment of the tetraacid with, for instance, glacial acetic acid and acetic anhydride, one can obtain the corresponding dianhydride of formula IV.

A more specific method for making the aforesaid bisimides of formula I comprises forming a mixture of the dihydroxy compound, for instance bisphenol-A, and sodium hydroxide in an aqueous medium with dimethyl sulfoxide (DMSO) and toluene. This mixture is heated to reflux to azeotropically remove water thereby producing an anhydrous dialkali metal salt. This salt is then reacted for a period of from 6 to 16 hours at about 60° C with the nitrophthalimide of formula II to give the crude aromatic bisimide. Thereafter the crude aromatic bisimide has to be washed several times with water, treated with, for instance, methanol several times to remove the impurities and the solid material is then washed again to obtain an aromatic bisimide of the desired purity, which can then be processed in a manner described above to form the dianhydride of formula IV, which in turn can be reacted with the organic diamine in the manner described in the aforesaid U.S. Pat. No. 3,847,867.

I have now discovered, unexpectedly that I am able to make the precursor aromatic bisimide of formula I, in situ (without prior preforming and isolation of the dianion), more expenditiously and with fewer steps by effecting reaction, under substantially anhydrous conditions, between a nitrophthalimide of formula II with an aromatic dihydroxy compound of formula III by employing a substantially anhydrous alkali-metal fluoride of a certain class and a specific class of solvents. By means of my process, many of the steps and undesirable features of the previous method for making the bisimides of formula I were eliminated or obviated. Whereas before dimethyl sulfoxide was necessary to help solubilize the dianion made from the aqueous sodium hydroxide and the dihydroxy aromatic compound and thus make its drying more complete, (incomplete drying greatly affected the purity of the bisimide produced), the use of water is almost completely eliminated. Moreover, the refluxing with the aqueous base additionally made the use of dimethyl sulfoxide necessary, since most other dipolar aprotic solvents contained functionalities which reacted with the aqueous base. Also, the necessity for azeotroping the formed water, which was timeconsuming and expensive, before the addition of nitroimide is substantially eliminated. Finally, before reaction could take place with the nitrophthalimide, the dianion salt had to be cooled before adding the nitrophthalimide and then again heated for at least 6 hours to insure complete reaction. By using my invention whereby a solid alkali-metal fluoride instead of an aqueous alkali-metal hydroxide is used with the dihydroxy aromatic compound and a dipolar aprotic solvent of a specific class is employed, the preparation of the bisimide proceeds readily with a minimum of steps.

Among the alkai-metal fluorides which can be employed are potassium fluoride, cesium fluoride, and rubidium fluoride. Sodium fluoride is unexpectedly ineffective in this reaction. The potassium and cesium fluorides are preferred since they give good results with minimal by-products. Preferably, the alkalimetal fluoride should be in as anhydrous a state as possible. Heating to remove residual moisture may be advisable to obtain the substantially anhydrous state prior to use. The alkalimetal fluoride can be in any form, such as powders or flakes, the important thing being that it is in a physical state which can permit ready reaction under the conditions of the above-described invention.

Among the nitrophthalimides which may be employed are for intance 3-, and 4-nitro-N-methylphthalimide, 3- and 4-nitro-N-ethylphthalimide, and 3- and 4-nitro-N-phenylphthalimide.

In addition to the aromatic dihydroxy compounds which are obvious from a reading of formula III, other dihydric phenols which may be employed are, for instance, 2,2-bis-(2-hydroxyphenyl)propane;
2,4'-dihydroxydiphenylmethane;
bis-(2-hydroxyphenyl)-methane; 2,2-bis-(4-hydroxyphenyl)-propane (hereinafter identified as "bisphenol-A" or "BPA")
1,1-bis-(4-hydroxyphenyl)-ethane;
1,1-bis-(4-hydroxyphenyl)-propane;
2,2-bis-(4-hydroxyphenyl)-pentane;
3,3-bis-(4-hydroxyphenyl)-pentane;
4,4'-dihydroxybiphenyl;
4,4'-dihydroxy-3,3',5,5'-tetramethylbiphenyl;
2,4-dihydroxybenzophenone;
4,4'-dihydroxydiphenyl sulfone;
2,4'-dihydroxydiphenyl sulfone;
4,4'-dihydroxydiphenyl sulfoxide;
4,4'-dihydroxydiphenyl sulfide;
4,4'-dihydroxydiphenyl oxide; etc.

In carrying out the reaction, one should employ at least 2 mols of the phthalimide of formula II, and preferably from 2.1 to 4 or more mols of the latter per mol of the aromatic dihydroxy compound of formula III. Too large a molar excess of the phthalimide will present problems of separation and recovery of the unused nitrophthalimide.

The amount of alkali-metal fluoride employed is not critically narrow and can be varied widely. Generally, I have found that at least two mols of the alkali-metal fluoride should be employed for each mol of the dihydric phenol, and preferably from about 2.05 to 3 mols of the former per mol of the dihydric phenol are advantageously used. Molar equivalents above 3 may be used but generally offer no advantages.

The amount of aprotic solvent used can also be varied widely but enough of the latter solvent should be used in order to form a liquid medium for effecting the reaction. On a weight basis, I have found it convenient to use from about 1 to 20 parts or more, by weight, of the aprotic solvent, per weight unit of the total weight of the two reactants, namely the nitrophthalimide of formula II and the dihydric phenol of formula III.

Although the above-described aprotic solvents can be employed alone in the practice of the invention, other inert cosolvents can be employed with the aprotic solvent. Generally the cosolvent used will assist (if this is desirable) in obtaining a high enough boiling point (about 100° to 200° C.) whereby refluxing of the reactants in the presence of the alkalimetal fluoride can be effected. The cosolvent used with the aprotic solvent is any solvent which is inert to the reactants or to the resulting reaction mixture and should boil above 100° C. Among such cosolvents may be mentioned the isomeric xylenes, such as m, o-, and p-xylene, toluene, chlorobenzene, bromobenzene, o-dichlorobenzene, anisole, ethylbenzene, mesitylene, octane, cycloheptane, diethyl and dimethyl ethers of ethylene glycol, etc. The inert cosolvent used should be generally liquid at room temperature, although this is not especially essential since it can also be a low melting solid which at reflux conditions or in the reaction mixture with the aprotic solvent forms a homogeneous solution. The cosolvent can have an additional function of insolubilizing the alkalimetal nitrite formed in the reaction and effectively removes the danger of the latter attacking the phthalimide ring and thus reducing the yield of desired bisimide of formula I.

The temperature at which reaction is carried out in the practice of my invention may be varied quite widely. Generally, I have found that temperatures from 100° to 200° C. are advantageously used. If lower temperatures are employed, the reaction goes at a slower pace, while if temperatures above 200° C. are employed one is apt to find that damaging side reactions may be going on causing a reduction in the yield of the desired bisimide.

The time of reaction may also be varied widely and only those times should be used which give optimum yields with a minimum of side reactions or loss of reactants or product. Generally I have found that the reaction goes to substantial completion within a period of from 1 to 10 hours or more.

When a cosolvent is used with the aprotic solvent, the amount of inert cosolvent can be varied widely. As in the case of using the aprotic solvent, the cosolvent should constitute on a weight basis of from 1 to 20 parts, or more of the cosolvent per part of the reactants used. On a volume basis, the aprotic solvent and the inert cosolvent can vary quite widely, and can be from about 30 to 70% of each of the solvents based on the total volume of the two solvents.

In all instances, substantially ahydrous conditions should be employed, and for best results an inert atmosphere should be employed such as conducting the reaction under a blanket of nitrogen. Stirring should be resorted to at all times in order to insure intimate contact of all the reactants and reagents required for optimum processing.

After the reaction is completed, the mixture can be added to a dilute aqueous HCl solution of about 0.01 to 1N HCl. The precipitate is either filtered or extracted with $CH_2Cl_2$ or any other suitable organic solvent, dried by various means, to yield the desired bisimide containing some impurities, which can be removed to yield the pure bisimide. The latter can be processed in the manner described previously to make the aforementioned dianhydrides.

In addition to the advantages recited previously, my process offers several additional advantages over previous methods for making the bisimide from the reaction of a dihydric phenol and a nitrophthalimide employing an alkali-metal hydroxide in the form of the dianion of the dihydric phenol. In the past, the dianion salt formed from the reaction of the dihydric phenol and the alkali-metal hydroxide had to be kept under an inert atmosphere to avoid rapid air-oxidation and had to be completely anhydrous before it could be allowed to undergo the aromatic nitro-displacement reaction to form the bisimide compound. This required a long period of time, for instance, from three to four days using a complex step of azeotropic distillation with toluene. Even after most of the water had been removed, it was necessary to scavenge the remaining amounts of water with dehydrating agents. Furthermore, once the dianion salt had been dried, two equivalents of the nitrophthalimide were added and the displacement reaction was then allowed to proceed for another period of time ranging from about 6 to 24 hours with ultimate additional workup required of the reaction product to isolate the desired bis-imide.

My nitro-displacement reaction is significantly simplified because I am able to generate substituted-phenoxide ions in situ with the alkali-metal fluoride in the presence of the nitrophthalimide, thus avoiding the need to prepare the dianion of the dihydric aromatic compound in advance. Thus, all the inredients can be placed in the reaction vessel at the same time, which simplifies the procedure and eliminates the later addition of nitro-imide.

In order that those skilled in the art may better understand how the present invention may be practiced, the following examples are given by way of illustration and not by way of limitation. All reactions were conducted using a reflux condenser under a nitrogen atmosphere with stirring.

EXAMPLE 1

A mixture of 5.529 grams (26.8 mmole) of 4-nitro-N-methylphthalimide, 2.735 grams (12.8 mmole) BPA, 1.596 grams (27.5 mmole) anhydrous powdered KF, and 50 ml anhydrous DMF was heated under a nitrogen atmosphere for 16 hours at the reflux temperature of the mass (about 153° C.). After cooling to room temperature (about 25° C.), the mixture was filtered to remove inorganic salts, and the filtrate was poured into 250 ml 0.2N aqueous HCl solution to remove DMF. Extraction with $CH_2Cl_2$ (two 150 ml portions), drying of the organic layer over anhydrous sodium sulfate and concentration in vacuum gave a product which contained 58% of the bisphenol-A bisimide (BPA-BI) of the formula

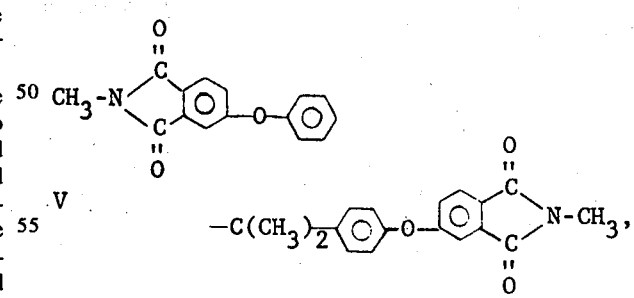

V

5% of the bisether

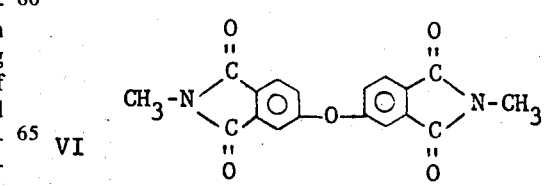

VI and 28% of the half addition product

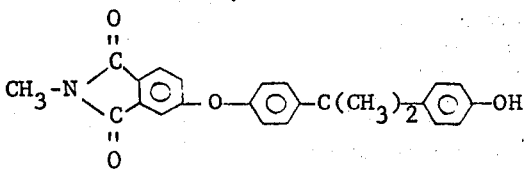

VII

EXAMPLE 2

In this example the conditions of reaction were repeated similarly as in Example 1 using 1.99 grams of BPA (8.73 mmole), 3.971 grams 4-nitro-N-methylphthalimide (19.3 mmole), 2.961 grams finely powdered cesium fluoride (19.5 mmole), 2.133 grams (21.33 mmole) $CaCO_3$ (used as desiccant), and 40 ml anhydrous DMF. The reaction mixture was heated at 153° C. for 5 hours and worked up similarly as described in Example 1 to give 2.972 grams (62% yield) of a solid consisting of BPA-BI with 7% thereof being the ether of formula VI.

EXAMPLE 3

Into a reaction vessel fitted with stirrer reflux condenser and nitrogen inlet, was placed 4.145 grams (0.02 mol) N-methyl-4-nitrophthalimide, 2.013 grams (0.009 mol) of BPA, 1.224 grams (0.021 mol) of anhydrous powdered potassium fluoride, and 40 ml dry dimethylsulfoxide. The mixture was stirred and heated at 145° for about 6 hours and then cooled to room temperature. The mixture which was obtained was poured into dilute aqueous hydrochloric acid (0.2N) and the resulting precipitate filtered off to yield 4.509 grams of a mixture, which when analyzed by $^{13}C$ nmr spectrum, showed the material to consist of 27% of the compound of formula VII, 11% of the ether of formula VI, and the balance being the BPA-BI of formula V.

It will of course be apparent to those skilled in the art that instead of using the nitrophthalimide of the foregoing examples, other nitrophthalimides, examples of which have been given above, can be employed in its place without departing from the scope of the invention. In addition, instead of employing the alkali-metal fluorides and the dihydric phenol recited in the previous examples, other akali-metal fluorides and dihydric phenols, many examples which have been recited previously, can be used in their place within the intended scope of the invention and with equivalent results. Finally, it will be apparent that the concentrations of ingredients and the conditions of reaction can also be varied widely as previously recited to obtain the desired aromatic bisimides expeditiously and usually in good yields.

As pointed out above, the aromatic bisimides obtained in accordance with the present invention may be hydrolyzed to the tetraacids and then dehydrated to form the dianhydrides which in turn can be reacted with various organic diamines such as metaphenylene diamine, 4,4'-diaminodiphenylmethane, benzidine, 4,4'-diaminodiphenylsulfone, 3,3'-dimethylbenzidine, etc., to yield resinous compositions which because of their desirable heat resistance can be employed in applications where elevated temperatures may be encountered. Thus, these polymeric compositions, whether filled or unfilled, can be employed in applications requiring good mechanical, electrical and heat resistance properties. They are eminently suitable for use in the manufacture of insulators, transformer blocks, motor armatures, printed circuits, honeycomb structure panels and compressor vanes, etc. In the form of solutions with suitable solvents, they can be used to coat electrical conductors such as copper or aluminum wire and the resinous materials so deposited can be heat-treated to effect conversion to the final polymerized state.

What I claim as new and desire to secure by Letters Patent is:

1. The process for making aromatic imides of the general formula

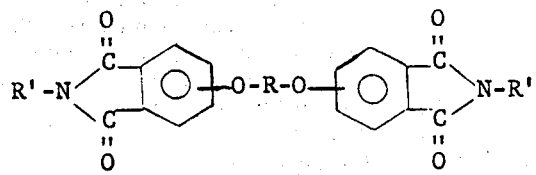

which comprises (1) effecting reaction under substantially anhydrous conditions between a nitrophthalimide of the general formula

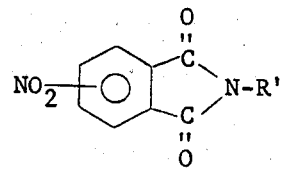

with a dihydroxy compound of the general formula
HO-R-OH
where R is a member selected from the class consisting of (a) divalent radicals of the formula

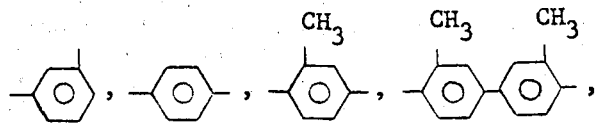

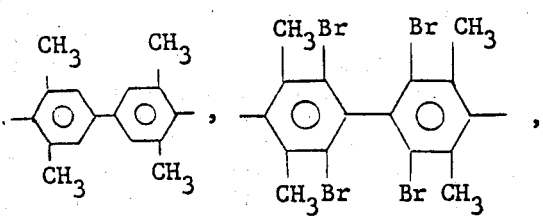

and

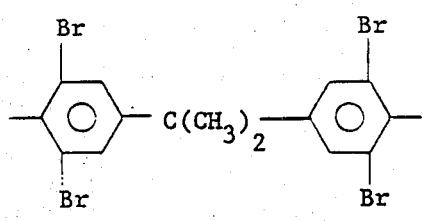

and (b) divalent organic radicals of the general formula

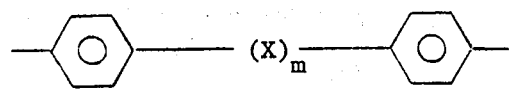

where X is a member selected from the class consisting of divalent radicals of the formulas

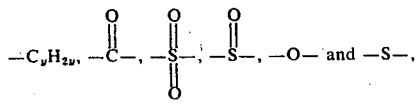

where $m$ is 0 or 1, $y$ is a whole number from 1 to 5, and R' is a phenyl radical or an alkyl radical of from 1 to 2 carbon atoms, the said reaction being conducted in a solvent selected from the class consisting of dimethyl sulfoxide, N,N-dimethyl formamide, N,N-dimethyl acetamide, N-methylpyrrolidone, and mixtures of such solvents and in the presence of a solid alkali-metal fluoride selected from the class consisting of cesium, potassium and rubidium fluorides, and mixtures thereof, and (2) isolating the formed aromatic bisimide.

2. The process as in claim 1 wherein the nitrophthalimide is 4-nitro-N-methylphthalimide.

3. The process as in claim 1 wherein the dihydroxy compound is bisphenol-A.

4. The process as in claim 1 wherein the alkalimetal fluoride is potassium fluoride.

5. The process as in claim 1 wherein the alkalimeta fluoride is cesium fluoride.

6. The process as in claim 1 wherein the solvent is N,N-dimethyl formamide.

7. The process for making a bisimide having the formula

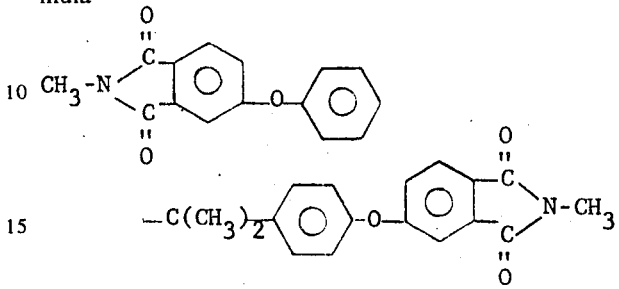

which comprises effecting reaction between 4-nitro-N-methylphthalimide and bisphenol-A in the presence of solid potassium fluoride using N,N-dimethyl formamide as the solvent, and isolating the formed bisimide.

8. The process as in claim 1 wherein at least 2 mols of the alkali-metal fluoride are employed per mol of the dihydroxy compound.

* * * * *